US00PP31148P2

(12) United States Plant Patent
Nelson et al.

(10) Patent No.: US PP31,148 P2
(45) Date of Patent: Dec. 3, 2019

(54) STRAWBERRY PLANT NAMED 'BG-9.3128'

(50) Latin Name: *Fragaria ananassa*
Varietal Denomination: BG-9.3128

(71) Applicant: Berry Genetics, Inc., Freedom, CA (US)

(72) Inventors: Steven D. Nelson, Watsonville, CA (US); Michael D. Nelson, Watsonville, CA (US); Leo W. Stoeckle, Moorpark, CA (US)

(73) Assignee: BERRY GENETICS, INC., Freedom, CA (US)

( * ) Notice: Subject to any disclaimer, the term of this patent is extended or adjusted under 35 U.S.C. 154(b) by 0 days.

(21) Appl. No.: 16/350,060

(22) Filed: Sep. 21, 2018

(51) Int. Cl.
*A01H 5/08* (2018.01)
*A01H 6/74* (2018.01)

(52) U.S. Cl.
USPC ..... Plt./208

(58) Field of Classification Search
USPC ..... Plt./156, 208, 209
See application file for complete search history.

*Primary Examiner* — Susan McCormick Ewoldt
*Assistant Examiner* — Karen M Redden
(74) *Attorney, Agent, or Firm* — Foley & Lardner LLP

(57) ABSTRACT

This invention relates to a new and distinct variety of strawberry plant named 'BG-9.3128'. This new strawberry plant named 'BG-9.3128' is primarily adapted to the growing conditions of the central coast of California, and is primarily characterized by its orange red fruit color, large fruit size, very good fruit flavor, early fruit production, small plant size, and short fruiting trusses with flowers typically held even with to below the foliage.

4 Drawing Sheets

Latin name: *Fragaria ananassa.*
Varietal denomination: 'BG-9.3128'.

BACKGROUND OF THE INVENTION

The present invention relates to a new and distinct strawberry variety named 'BG-9.3128'. This new variety is a result of a controlled cross made in 2009 in an ongoing breeding program between strawberry variety designated 'BG-4.352' (U.S. Plant Pat. No. 26,921) as the seed (female) parent, and strawberry variety designated 'BG-1975' (U.S. Plant Pat. No. 17,725) as the pollen (male) parent. The variety is botanically known as *Fragaria ananassa.*

The seedling resulting from the aforementioned cross was selected from a controlled breeding plot in Ventura County, Calif. in the winter of 2011. After its selection, the new variety was asexually propagated by stolons in both Siskiyou County, Calif. and San Joaquin County, Calif. The new variety was extensively tested over the next several years in fruiting fields in Ventura County, Calif. This propagation has demonstrated that the combination of traits disclosed herein as characterizing the new variety are fixed and remain true-to-type through successive generations of asexual reproduction.

BRIEF SUMMARY OF THE INVENTION

'BG-9.3128' is primarily adapted to the climate and growing conditions of the central coast of California. The nearby Pacific Ocean provides the humidity and moderate temperatures needed to produce a strong, vigorous plant and maintain fruit quality during the winter and spring production months.

The following traits have been repeatedly observed and are determined to be unique characteristics of 'BG-9.3128', which in combination distinguish this strawberry plant as a new and distinct variety:

1. Orange red fruit color;
2. Large fruit size;
3. Very good fruit flavor;
4. Early fruit production;
5. Small plant size; and
6. Short fruiting trusses with flowers typically held even with to below the foliage.

The strawberry variety that is believed to be most closely related to the new variety 'BG-9.3128' is 'BG-959' (U.S. Plant Pat. No. 17,864). In side-by-side comparisons to the similar strawberry variety 'BG-959', 'BG-9.3128' differs by the following combination of characteristics as described in Table 1.

TABLE 1

| Characteristic | 'BG-9.3128' | 'BG-959' (U.S. Plant Pat. No. 17,864) |
|---|---|---|
| Fruit: color | Orange red | Red |
| Fruit: size | Large | Medium |
| Fruit: flavor | Very good | Fair |
| Fruit: firmness of flesh | Firm | Ranges from medium to firm |
| Foliage: color | Ranges from medium to light green | Ranges from medium to dark green |
| Foliage: gloss | Absent or very weak | Ranges from medium to strong |
| Foliage: interveinal blistering | Absent or very weak | Ranges from medium to strong |
| Stipule: anthocyanin intensity | Absent or very weak | Strong |

For identification, a series of molecular markers have been determined for this new variety.

'BG-9.3128' differs from its parents, 'BG-4.352' and 'BG-1975' by the following combination of characteristics as described in Tables 2 and 3.

TABLE 2

| Characteristic | 'BG-9.3128' | 'BG-4.352' U.S. Plant Pat. No. 26,921) |
|---|---|---|
| Marketable yield (gm/plt) | 850 | 1,000 |
| Fruit: color | Orange red | Red |
| Fruit: insertion of achenes | Level with the surface | Ranges from level with to below the surface |
| Fruit: firmness of flesh | Firm | Medium |
| Fruit: flavor | Very good | Fair |
| Fruiting truss: position relative to foliage | Ranges from level with to beneath | Ranges from level with to above |

TABLE 3

| Characteristic | 'BG-9.3128' | 'BG-1975' (U.S. Plant Pat. No. 17,725) |
|---|---|---|
| Fruit: size | Large | Medium |
| Fruit: color | Orange red | Ranges from red to orange red |
| Fruit: insertion of achenes | Level with the surface | Below the surface |
| Plant: size | Small | Ranges from medium to large |
| Fruiting truss: position relative to foliage | Ranges from level with to beneath | Ranges from level with to above |

BRIEF DESCRIPTIONS OF THE PHOTOGRAPHS

The accompanying color photographs illustrate the overall appearance of typical specimens of the new strawberry variety 'BG-9.3128' at various stages of development, as true as it is reasonably possible with color reproductions of this type. Color in the photographs may differ slightly from the color value cited in the botanical descriptions which accurately describe the color of 'BG-9.3128'. The depicted plant and plant parts of the new strawberry variety 'BG-9.3128' are approximately six months old. The photographs were taken in Ventura County, Calif.

DETAILED BOTANICAL DESCRIPTION

Figure 1:
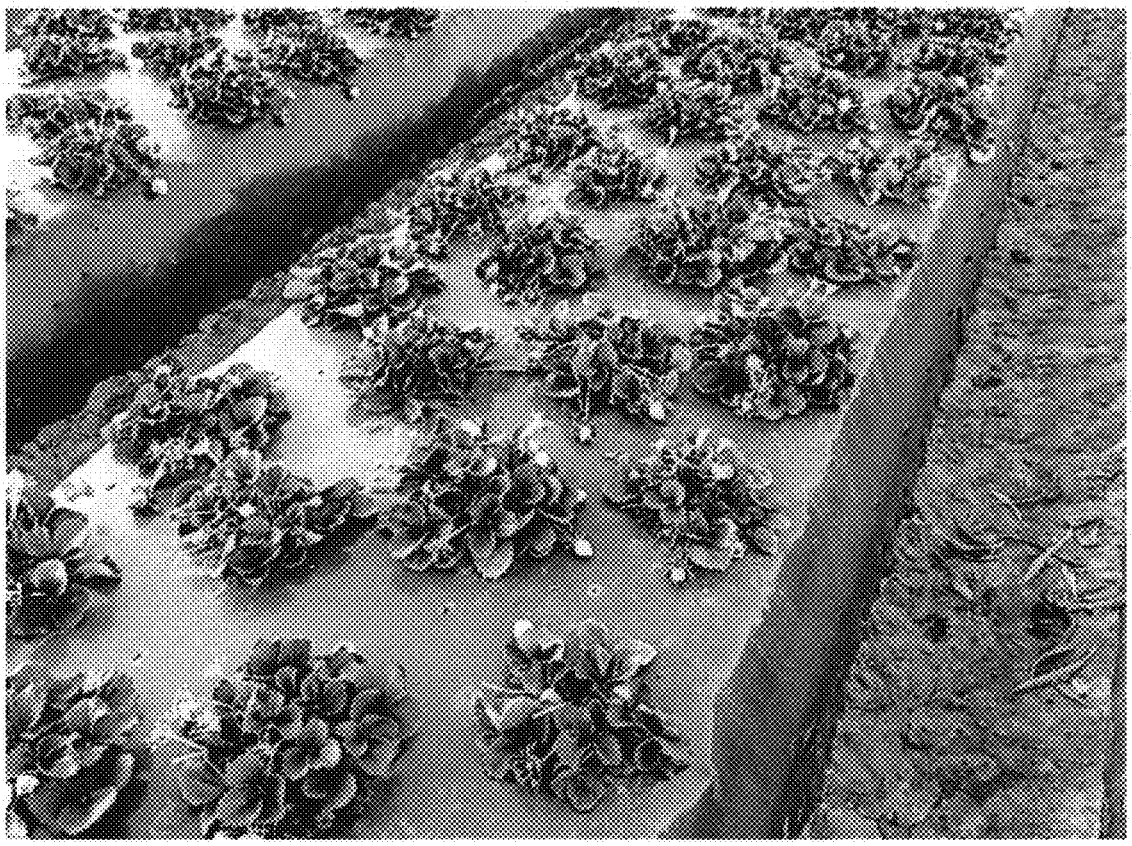
FIG. 1 shows typical fruiting field characteristics of 'BG-9.3128', taken in the month of March 2018.
Figure 2:
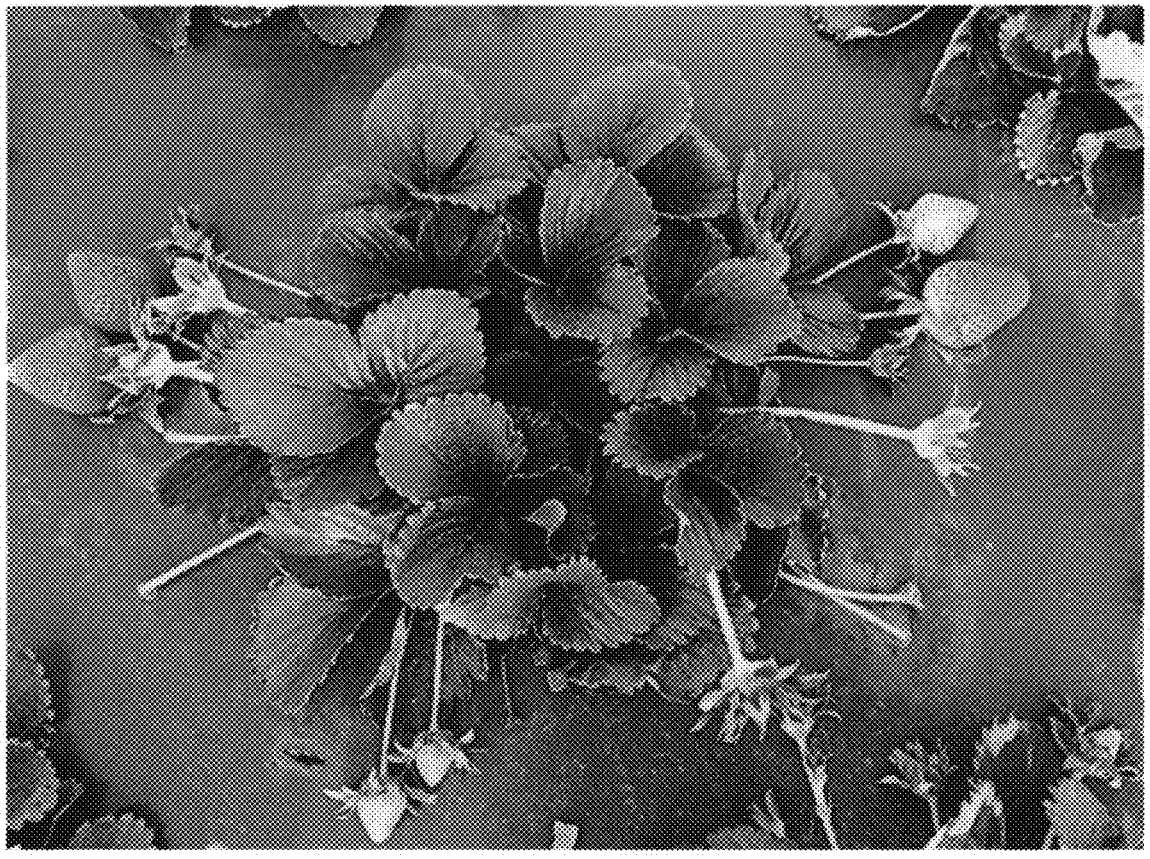
FIG. 2 shows a close-up view of a typical plant of 'BG-9.3128', taken in the month of March 2018.
Figure 3:
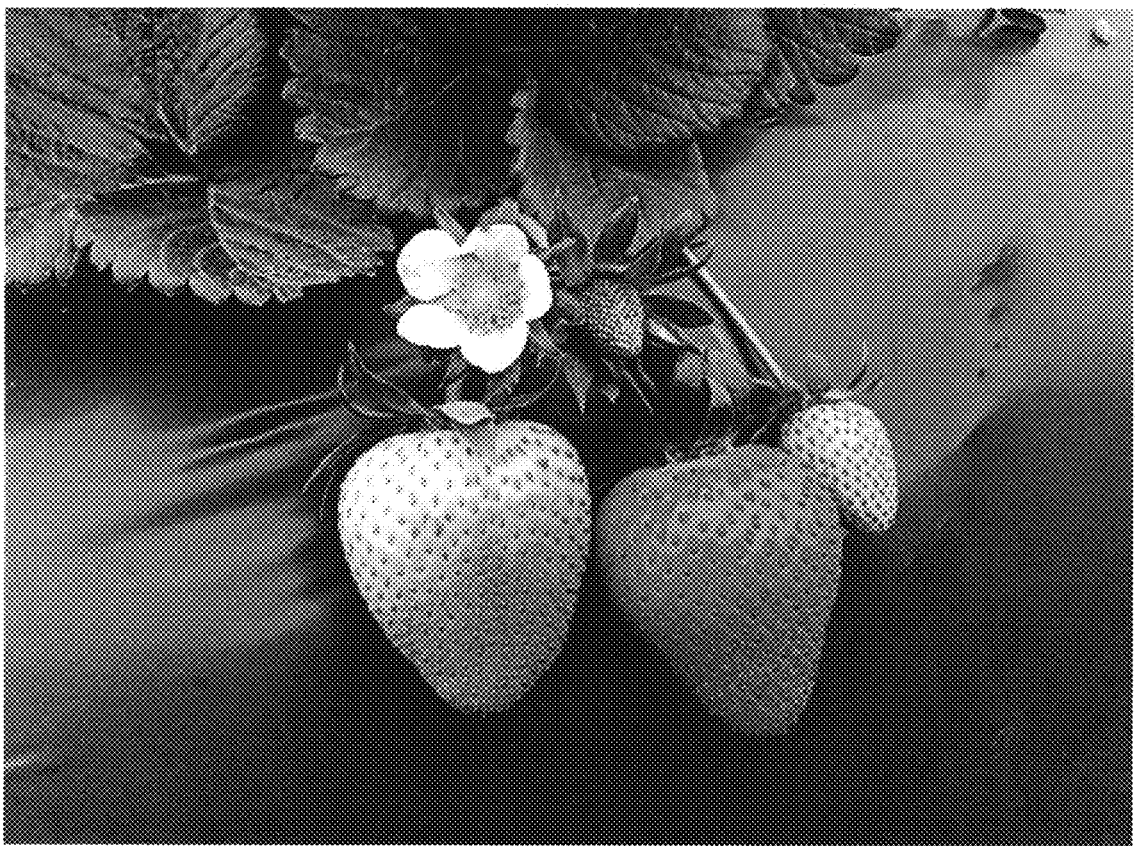
FIG. 3 shows typical mature and immature field fruit of 'BG-9.3128', taken in the month of March 2018.
Figure 4:
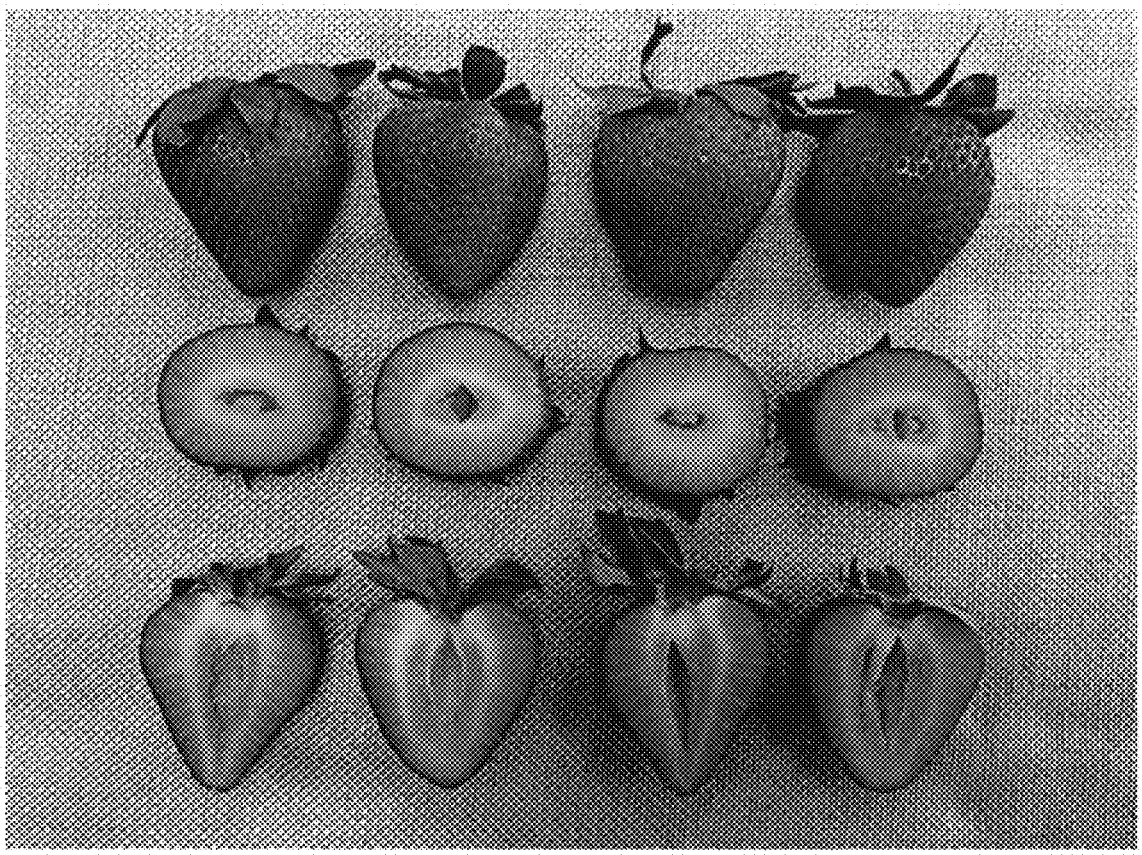
FIG. 4 shows typical internal and external mature fruit characteristics of 'BG-9.3128', taken in the month of March 2018.

The new variety 'BG-9.3128' has not been observed under all possible environmental conditions. The characteristics of the new variety 'BG-9.3128' may vary in detail, depending upon variations in environmental factors, including weather (temperature, humidity and light intensity), day length, soil type and location. In addition, the characteristics of any parental variety or comparison variety included in Tables 1, 2 and 3 of the present invention may vary in detail, depending upon variations in environmental factors, including weather (temperature, humidity and light intensity), day length, soil type and location.

The aforementioned photographs, together with the following description of the new variety 'BG-9.3128', unless otherwise noted, are based on observations taken during the 2018 growing season in Ventura County, Calif. These measurements and ratings were taken from plants of 'BG-9.3128' dug from a high-elevation nursery located in Siskiyou County, Calif. during early October 2017 and planted approximately four to five days later in Ventura County, Calif. The approximate age of the observed plants is six months. Yield observations including average weight and marketable yield, along with fruit quality characteristics including soluble solids, are averaged from four years of data collected from the 2015 through 2018 growing seasons. Flower measurements and characteristics are from secondary flowers unless otherwise noted. Fruit characteristics and measurements are from secondary fruit, unless otherwise noted.

Where noted, color terminology follows The Royal Horticultural Society Colour Chart, London (2007).

The following characteristics describe fruit, plant, stolon, foliage, fruiting truss, flower, reproductive organs and pest and disease characteristics of the new strawberry 'BG-9.3128'.

Fruit characteristics:

*Color of mature fruit*.—RHS 34A (orange red).

*Color of internal flesh (excluding core)*.—RHS 45C (medium red).

*Color of core*.—RHS 39A (medium red).

*Average length (cm)*.—4.5.

*Average width (cm)*.—3.9.

*Size*.—Large.

*Average length/width ratio*.—1.17 (slightly longer than broad).

*Average calyx diameter (cm)*.—5.4.

*Season average weight (gm)*.—28.8.

*Achene color, shaded side*.—RHS 153B (yellow green group).

*Achene color, sun-exposed side*.—RHS 182A (greyed red group).

*Average achene weight (mg)*.—0.48.

*Average achenes per berry*.—414.

*Season marketable yield (gm/plant)*.—862.

*Predominant shape*.—Cordate (cordiform).

*Difference in shape between primary and secondary fruit*.—Ranges from slight to moderate.

*Band without achenes*.—Narrow.

*Evenness of surface*.—Even or very slightly uneven.

*Evenness of color*.—Even or very slightly uneven.

*Glossiness*.—Ranges from medium to strong.

*Insertion of achenes*.—Level with surface.

*Position of calyx attachment*.—Level.

*Attitude of sepals*.—Ranges from outward to upward.

*Size of calyx in relation to fruit diameter*.—Ranges from slightly larger to much larger.

*Adherence of calyx (when fully ripe)*.—Strong.

*Firmness of flesh*.—Firm.

*Distribution of red color of the flesh*.—Marginal and central.

*Hollow center expression*.—Ranges from moderate to strong.

*Flavor*.—Very good.
*Soluble solids* (% *Brix*).—7.2.
*Time of first flowering*.—Very early (December in Ventura County, Calif.).
*Time of first fruit*.—Very early (Late December in Ventura County, Calif.).
*Harvest period*.—Late December to June (in Ventura County, Calif.).
*Harvest maturity*.—Early season (February to March).
*Type of bearing*.—Not remontant.

Plant characteristics:
*Average height* (*cm*).—11.0.
*Average spread* (*cm*).—28.7.
*Size*.—Small.
*Habit*.—Semi-upright.
*Density*.—Medium.
*Vigor*.—Medium.

Stolon characteristics:
*Color*.—RHS 146D (yellow green group).
*Anthocyanin coloration*.—RHS 181B (greyed red group).
*Anthocyanin intensity*.—Strong.
*Pubescence*.—Medium.
*Attitude of hairs*.—Upward.
*Average quantity in nursery* (*per square foot*).—5 to 6 (medium).
*Average diameter at the bract* (*mm*).—3.3 (medium).

Terminal leaflet characteristics:
*Average length* (*cm*).—5.5.
*Average width* (*cm*).—5.0.
*Average length/width ratio*.—1.10 (longer than broad).
*Shape of base*.—Obtuse.
*Margins* (*shape of teeth*).—Obtuse (serrate to crenate).
*Average serrations per leaf*.—19.8.

Foliage characteristics:
*Color of upper surface*.—RHS 146B (ranges from light yellow green to medium yellow green).
*Color of underside*.—RHS 147B (yellow green group).
*Number of leaflets*.—3.
*Leaf size*.—Small.
*Average area terminal* ($cm^2$).—27.7.
*Average length* (*cm*).—8.7.
*Average width* (*cm*).—10.5.
*Average area foliage* ($cm^2$).—91.3.
*Shape in cross section*.—Ranges from slightly concave to flat.
*Interveinal blistering*.—Ranges from absent or weak to medium.
*Leaf glossiness*.—Absent or weak.
*Leaf variegation*.—Absent.

Petiole characteristics:
*Petiole color*.—RHS 146C (yellow green group).
*Average length* (*cm*).—7.5.
*Average diameter* (*mm*).—2.8.
*Petiolule color*.—RHS 146C (yellow green group).
*Petiolule average length* (*mm*).—4.7.
*Attitude of hairs*.—Strongly outward.
*Frequency of bract leaflets*.—Few (10-20% occurrence).
*Size of bract leaflets*.—Small.
*Pubescence*.—Heavy.

Stipule characteristics:
*Color*.—RHS 146B (yellow green group).
*Anthocyanin coloration*.—RHS 61C (red purple group).
*Anthocyanin intensity*.—Absent or very weak.
*Average length* (*mm*).—18.3.
*Average width* (*mm*).—9.2.

Fruiting truss characteristics:
*Anthocyanin coloration*.—RHS 181C (greyed red group).
*Anthocyanin intensity*.—Ranges from weak to medium.
*Average length at maturity* (*cm*).—19.4.
*Position relative to foliage*.—Ranges from beneath to level with.
*Flower quantity* (*average per plant*).—30 to 35 (medium).
*Pedicel attitude of hairs*.—Strongly outward.
*Pubescence*.—Ranges from medium to strong.
*Attitude at first pick*.—Prostrate.

Flower characteristics:
*Petal color*.—RHS NN155C (white group).
*Sepal color*.—RHS 138A (green group).
*Corolla* (*flower*) *average diameter* (*mm*).—29.5 (large).
*Calyx average diameter* (*mm*).—36.3.
*Petal average length* (*mm*).—11.5.
*Petal average width* (*mm*).—11.0.
*Petal average length/width ratio*.—1.04 (ranges from as long as broad to longer than broad).
*Average petals per flower*.—6.2.
*Sepal average length* (*mm*).—14.0.
*Sepal average width* (*mm*).—5.2.
*Sepal average length/width ratio*.—2.72.
*Average sepals per flower*.—12.3.
*Size of calyx relative to corolla*.—Larger.
*Size of inner calyx relative to outer calyx*.—Same.
*Relative position of petals* (*flowers with* 5 *or* 6 *petals*).—Overlapping.

Reproductive organs:
*Receptacle color*.—RHS 147C (yellow green group).
*Pollen color*.—RHS 14A (yellow orange group).
*Stamen*.—Present.
*Pollen amount*.—Abundant.

Disease and pest reactions:
*Powdery mildew* (*Sphaerotheca macularis*).—Moderate.
*Angular leaf spot* (*Xanthomonas fragariae*).—Susceptible.
*Botrytis fruit rot* (*Botrytis cinerea*).—Moderately susceptible.
*Fusarium wilt* (*Fusarium oxysporum*).—Resistant.
*Anthracnose crown rot* (*Colletotrichum fragariae*).—Susceptible.
*Two-spotted spider mite* (*Tetranychus urticae*).—Moderately susceptible.

We claim:

1. A new and distinct strawberry plant named 'BG-9.3128', as herein described and illustrated by the characteristics set forth above.

* * * * *